United States Patent [19]

Fujimoto et al.

[11] Patent Number: 5,466,720

[45] Date of Patent: Nov. 14, 1995

[54] METHOD OF PRODUCING DIMETHYL ETHER

[75] Inventors: Kaoru Fujimoto, 18-1-1031, Minami-Ooi 6-chome, Shinagawa-ku, Tokyo 140; Tsutomu Shikada, Tokyo; Yojiro Yamaoka, Tokyo; Takashi Sumigama, Tokyo, all of Japan

[73] Assignees: Kaoru Fujimoto; NKK Corporation, Tokyo, both of Japan

[21] Appl. No.: 321,521

[22] Filed: Oct. 12, 1994

Related U.S. Application Data

[63] Continuation of Ser. No. 87,757, filed as PCT/JP92/01467, Jul. 9, 1993, Pat. No. 5,389,689.

[30] Foreign Application Priority Data

Nov. 11, 1991 [JP] Japan .................................. 3-294630
Nov. 11, 1991 [JP] Japan .................................. 3-294631

[51] Int. Cl.$^6$ .................................................. C07C 41/01
[52] U.S. Cl. .......................................... 518/700; 518/713
[58] Field of Search ..................................... 518/700, 713

[56] References Cited

U.S. PATENT DOCUMENTS 5,218,003  6/1993  Lewnard et al. ...................... 518/700
5,389,689  2/1995  Fujimoto et al. ...................... 518/700

FOREIGN PATENT DOCUMENTS 0324475  7/1989  European Pat. Off. .
0409086  1/1991  European Pat. Off. .
0483609  5/1992  European Pat. Off. .

*Primary Examiner*—Werren B. Lone
*Attorney, Agent, or Firm*—Sughrue, Mion, Zinn, Macpeak & Seas

[57] ABSTRACT

In a method of producing dimethyl ether from a mixed gas containing carbon monoxide and either or both of hydrogen and water vapor or a mixed gas of them further containing carbon dioxide, the improvement which comprises using a mixed catalyst prepared by pulverizing a mixed catalyst containing at least zinc oxide, copper oxide or chromium oxide, and aluminum oxide, compressing to bind them by a high pressure press and then pulverizing again or a mixed catalyst comprising at least zinc oxide, copper oxide and alumina, in a slurry state formed by suspending in a solvent. In the method of the invention, the yield of dimethyl ether is high, and the conversion water produced through reaction to hydrogen is high. There is no problem of clogging with catalyst, and mechanical strength is not required. Besides, the applicable range of the ratio of carbon monoxide and hydrogen is wide and the reaction is possible in the presence of carbon dioxide in a high concentration. Moreover, affects by impurities and catalyst poisons are small.

3 Claims, No Drawings

METHOD OF PRODUCING DIMETHYL ETHER

This is a continuation of application No. 08/087,757 filed as PCT/JP92/01467, Jul. 9, 1993, now U.S. Pat. No. 5,389,689.

TECHNICAL FIELD

The invention relates to a method of producing dimethyl ether from a mixed gas containing carbon monoxide and either or both of hydrogen and water vapor, or a mixed gas of them further containing carbon dioxide.

BACKGROUND ART

Heretofore, some methods have been known for the production of dimethyl ether from a mixed gas composed of carbon monoxide, carbon dioxide and hydrogen.

For example, Japanese Patent KOKOKU 54-32764 discloses a method of producing dimethyl ether by loading a mixture of a methanol synthesis catalyst made of copper carried on alumina and a methanol dehydration catalyst made of zinc and chromium carried on alumina into a reactor or loading them into layers alternately into a reactor and supplying a mixed gas composed of carbon monoxide, carbon dioxide and hydrogen thereto. Besides, Japanese Patent KOKOKU 61-43332 discloses a method of producing dimethyl ether using a catalyst composed of a mixture of oxides of copper, zinc, chromium and aluminum treated with a silicon compound such as tetraethyl orthosilicate so as to resist heat, high temperature stream and mechanical stress and then molded. Moreover, Japanese Patent KOKAI 3-181435 discloses a method of producing dimethyl ether characteristic in the use of a catalyst in a slurry state formed by suspending in a solvent, in a method of producing dimethyl ether from a mixed gas of carbon monoxide and hydrogen or a mixed gas them further containing carbon dioxide and/or water vapor.

The above conventional method of producing dimethyl ether had some problems as follows:

As to the catalyst composed of oxides of copper, zinc, chromium and aluminum, the mechanical strength of catalyst particles is insufficient and the catalyst particles are gradually powdered by the action of gas fluid, heat, etc. which pass through the catalyst layer at a high speed resulting in the occurrence of clogging of the catalyst layer.

Besides, it was also a problem that the water by-produced at the time of producing dimethyl ether from methanol reacts with the oxides of aluminum to degrade the strength.

Moreover, since the catalytic activity of the catalyst is gradually decreased with the passage of reaction time, when the catalytic activity is decreased, it is necessary to be regenerated. Accordingly, the catalyst must be taken out from the reactor and then regenerated. However, it was especially troublesome to take out the catalyst.

Furthermore, since the method of synthesizing dimethyl ether from carbon monoxide and hydrogen is an extremely great exothermic reaction, the method had a problem that partial heating is liable to occur and it is not easy to maintain and control the reaction temperature uniform.

The present invention has been made in order to solve the above mentioned problems of the prior art and further to improve the method described in Japanese Patent KOKAI 3-181435 which the inventors previously developed, and an object of the invention is to provide a method of producing dimethyl ether wherein, mechanical strength is not required for the catalyst, taking out and regeneration of the catalyst are easy, and the removal of reaction heat and the control of reaction temperature are also easy.

DISCLOSURE OF THE INVENTION

The present invention has been made in order to achieve the above object and is constituted by that, in a method of producing dimethyl ether from a mixed gas containing carbon monoxide and either or both of hydrogen and water vapor or a mixed gas of them further containing carbon dioxide, the improvement which comprises using a mixed catalyst prepared by pulverizing a mixed catalyst containing at least zinc oxide, copper oxide or chromium oxide, and aluminum oxide, compressing to bind them by a high pressure press and then pulverizing again or a mixed catalyst comprising at least zinc oxide, copper oxide and alumina, in a slurry state formed by suspending in a solvent.

BEST MODE FOR CARRYING OUT THE INVENTION

The solvent used in the invention may be anyone capable of becoming in a liquid state under reaction conditions. For example, aliphatic, aromatic and alicyclic hydrocarbons, alcohols, ethers, esters, ketones and halides and mixtures thereof, etc. can be used.

Besides, gas oil from which sulfur components were removed, vacuum gas oil and high boiling point fractions of coal tar which were hydrogenated can also be used.

The catalyst used in the invention is a combination of a known methanol synthesis catalyst, methanol dehydration catalyst and water gas shift catalyst. As the methanol synthesis catalyst, there are copper oxide-zinc oxide, zinc oxide-chromium oxide, and the like. As the methanol dehydration catalyst, there are $\gamma$-alumina, silica.alumina, zeolite, etc. The metal oxide components of zeolite are oxides of alkali metal, such as sodium, potassium, etc., oxides of alkaline earth metal, such as calcium, magnesium, etc., and the like. As the water gas shift catalyst, there are copper oxide-zinc oxide, iron oxide-chromium oxide, etc. Methanol synthesis catalyst is an excellent water gas shift catalyst, and can be combined the water gas shift catalyst. As a catalyst combining the methanol dehydration catalyst and the water gas shift catalyst, copper oxide carried on alumina catalyst can be used.

The mixing ratio of the above methanol synthesis catalyst, methanol dehydration catalyst and water gas shift catalyst is not particularly limited, and is suitably selected in accordance with the kind of each component, reaction conditions or so on. However, in most cases, a suitable range of the methanol dehydration catalyst is in about 0.1 to 5, preferably about 0.2 to 2, and that of the water gas shift catalyst is in about 0.2 to 5, preferably about 0.5 to 3, per 1 part of the methanol synthesis catalyst at a ratio by weight. When the methanol synthesis catalyst is combined with the water gas shift catalyst, the amount of the above water gas shift catalyst is added to the amount of the methanol synthesis catalyst.

The above catalyst is co-pulverized, i.e. pulverized in a mixed state. A pulverization degree is about 0.1 to 20 μm, preferably about 0.5 to 10 μm in grain size. Subsequently, the co-pulverized material is pressed to adhere to each other. The pressure is in the range capable of adhering copulverized material by compression, and usually, it is about 100 to 500 kg/cm². The pressing may be conducted by a high-pressure press, etc. Subsequently, the compressed adhered material is pulverized again. The pulverization may be conducted up to about 1 to 300 μm, preferably about 10 to 150 μm in grain size. The pulverized material can be used as the catalyst as it is, optionally subjected to activation treatment, but it may be screened, if necessary. Besides, when respective oxides are in an insufficient uniform dispersion state, it is a matter of course that the compression and pulverization can be repeated again.

The copper oxide carried on alumina catalyst used as the methanol dehydration catalyst combined with the water gas shift catalyst can be produced by a conventional common method used for the production of these kind catalysts. For example, the sedimentation method, the impregnation method, etc. can be used. Besides, as raw materials for the production of catalyst, nitrate, carbonate, organic acid salt, halide, hydroxide or the like of copper and nitrate, carbonate, organic acid salt, aluminate, hydroxide, oxide or the like of aluminum are usable. The ratio of copper oxide which is carried on alumina carrier is about 0.5 to 50, preferably about 1 to 20 of copper oxide per 100 of alumina at a ratio by weight.

The mixing ratio of the above methanol synthesis catalyst and copper oxide carried on alumina catalyst is not particularly limited, and is suitably selected in accordance with the kind of each component or reaction conditions, etc. However, in most cases, a suitable range is in about 1:20 or 20:1, preferably about 1:10 to 10:1 at a ratio by weight.

Both of the above catalysts are used as powder, and a suitable mean grain size is not more than 300 μm, preferably about 1 to 200 μm, particularly preferably about 10 to 150 μm. For that purpose, they can be further pulverized, if necessary. Although both catalysts can be mixed after pulverization, it is preferable to co-pulverizing them.

The amount of catalyst to exist in solvent is suitably set in accordance with the kind of the solvent, reaction conditions and the like, and it is usually about 1 to 50 wt. %, preferably 2 to 30 wt. %, per the solvent.

Since carbon monoxide and hydrogen are once dissolved in a solvent and then contacted the catalyst, the mixing ratio of hydrogen and carbon monoxide is applicable in a wide range. For example, those having a mixing ratio of 20 to 0.1, preferably 10 to 0.2, as $H_2/CO$ molar ratio are usable. On the other hand, in the case of a mixed gas having a very small ratio (e.g. not more than 0.1) of hydrogen and carbon monoxide ($H_2/CO$ ratio) or carbon monoxide not containing hydrogen, it is necessary to convert a part of carbon monoxide to hydrogen and carbon dioxide in a reactor by supplying stream separately. Besides, since the composition of raw material gas is not always consistent with the composition on the surface of catalyst due to the presence of solvent between the raw material gas and the catalyst, carbon dioxide may exist in the mixed gas of carbon monoxide and hydrogen or the carbon monoxide gas in a relatively high concentration (e.g. 20 to 50%). Furthermore, in the method of the invention, even if the raw material gas contains components acting as catalyst poison such as sulfur compounds such as hydrogen sulfide, cyanogen compounds such as hydrogen cyanide, chlorine compounds such as hydrogen chloride, and the like, their affects on the catalyst are sharply reduced compared with the vapor phase-solid phase contact method. Even when the catalyst is poisoned to decrease the activity by taking out slurry from the reactor and putting with pressure a new slurry containing the catalyst having a high activity, the productivity of the reactor can be maintained constant as a whole.

By streaming a mixed gas composed of carbon monoxide and hydrogen in the above catalyst-solvent slurry, dimethyl ether can be obtained by a high yield. In order to dissolve the mixed gas into the solvent efficiently, the mixed gas is blown into the solvent and optionally stirred by a stirrer or the like. As the reaction conditions, a preferable reaction temperature is 150° to 400° C., particularly preferably 200° to 350° C. When the reaction temperature is lower than 150° C. or higher than 400° C., the conversion of carbon monoxide decreases. The reaction heat can be recovered as medium pressure stream by providing a cooling coil in a reactor and passing hot water thereto. Thereby, the reaction temperature can be controlled freely. A preferable reaction pressure is 10 to 300 kg/cm², particularly preferably 15 to 150 kg/cm². When the reaction pressure is lower than 10 kg/cm², the conversion of carbon monoxide is low. When it is higher than 300 kg/cm², the reactor is a special one and it is disadvantageous in economical viewpoint because of requiring a lot of energy for raising pressure. Space velocity (feeding speed of mixed gas in the normal condition per 1 kg of catalyst) is preferably 100 to 50000 l/kg·h, particularly preferably 500 to 30000 l/kg·h. When the space velocity is greater than 50000 l/kg·h, the conversion of carbon monoxide is low. When it is smaller than 100 l/kg·h, the reactor is extremely bulky and it is uneconomical.

The distance between various catalysts can be remarkably close by co-pulverizing the methanol synthesis catalyst, methanol dehydration catalyst and water gas shift catalyst, compressing to adhere them, and pulverizing again. As a result, the reaction cycle mentioned below proceeds rapidly to improve the yield of dimethyl ether. That is, in this reaction process, first, methanol is produced from carbon monoxide and hydrogen on the methanol synthesis catalyst, and subsequently the methanol moves onto the methanol dehydration catalyst to produce dimethyl ether and water by dehydration condensation. Furthermore, the water moves onto the water gas shift catalyst and/or the methanol synthesis catalyst, and reacts with carbon monoxide to produce carbon dioxide and hydrogen.

Reaction formulas are as follows.

$$CO + 2H_2 \rightarrow CH_3OH \tag{1}$$

$$2CH_3OH \rightarrow CH_3OCH_3 + H_2O \tag{2}$$

$$CO + H_2O \rightarrow CO_2 + H_2 \tag{3}$$

In the case of the combination of the methanol synthesis catalyst and the copper oxide carried on alumina catalyst, the methanol produced from carbon monoxide and hydrogen on the methanol synthesis catalyst moves onto the copper oxide carried on alumina catalyst, and the methanol condensates with dehydration by the catalytic action of alumina to produce dimethyl ether and water. Furthermore, the water reacts with the carbon monoxide on the copper oxide carried on alumina catalyst to convert to carbon dioxide and hydrogen. Hereupon, if alumina catalyst is used without co-pulverization instead of the copper oxide carried on alumina catalyst, water produced on the alumina is once dissolved into the solvent, and moves in the solvent to arrive onto the methanol synthesis catalyst again then the reaction of formula (3) proceeds. However, there is also a sufficiently high possibility that the water dissolved in the solvent escapes into vapor phase and is released out of the reaction system together with dimethyl ether. In this case, a high conversion rate of water can not be obtained. If a catalyst (copper oxide), which progresses the reaction of formula (3), exists very close to the alumina, water reacts with carbon monoxide without dissolving into the solvent to obtain a high conversion rate of water, and the reaction cycle proceeds smoothly.

In the reaction system, since the mixed gas contacts the catalyst after dissolving carbon monoxide and hydrogen into the solvent without contacting the mixed gas with the catalyst directly like the vapor phase-solid phase contact reaction, it is possible to achieve a constant composition of carbon monoxide and hydrogen in the solvent to supply them onto the surface of the catalyst irrespective of the composition of gas by selecting the solvent taking the solubility of carbon monoxide and hydrogen into consideration. Accordingly, the mixing ratio of hydrogen and carbon monoxide ($H_2$/CO ratio) is applicable in a wide range. Besides, the reaction of carbon monoxide and water by-produced upon producing dimethyl ether is accelerated by the water gas shift catalyst or the copper oxide carried on alumina catalyst to increase the supply amount of hydrogen onto the surface of the methanol synthesis catalyst. It is considered that this is also a reason for the usability of $H_2$/CO gas in a wide mixing ratio range.

EXAMPLES

I. Preparation of Catalyst

EXAMPLES 1 to 4

100 g of commercial Cu—Zn methanol synthesis catalyst (BASF, S3-85) and 50 g of γ-alumina (Reference Catalyst of Catalysis Soc. Japan, ALO-4) calcined for 2 hours at 500° C. in the air were co-pulverized for about 3 hours in a ball mill into fine powder having about not more than 20 μm in grain size. Subsequently, the powder was compressed to adhere at 300 kg/cm² by a high pressure press for about 24 hours, and then pulverized again by the ball mill for about 3 hours to obtain a catalyst in fine powder form of not more than about 120 μm.

COMPARATIVE EXAMPLE 1

In the above example, a catalyst in fine powder form of not more than about 120 μm was prepared by only co-pulverizing without compressing to adhere.

EXAMPLES 5, 9, 10

15.7 g of copper acetate ($Cu(CH_3COO)_2 \cdot H_2O$) was dissolved in 200 ml of water, 95 g of γ-alumina (Reference Catalyst of Catalysis Soc. Japan, ALO-4) was put therein followed by evaporating to dryness. Subsequently, this was dried for 24 hours at 120° C. in the air, and then, calcined for 4 hours at 500° C. in the air to obtain a catalyst. The composition was CuO:$Al_2O_3$=6.2:93.8 (weight ratio).

Subsequently, 50 g of the above CuO—$Al_2O_3$ catalyst and 100 g of commercial Cu—Zn methanol synthesis catalyst (ICI, 51-2) were co-pulverized for about 3 hours in a ball mill to obtain a catalyst in fine powder form of not less than about 120 μm in grain size.

EXAMPLES 6, 11, 12

Using 31.4 g of copper acetate, CuO—$Al_2O_3$ catalyst was prepared by the same method as Example 5. The catalyst obtained was CuO:$Al_2O_3$=11.6:88.4 (weight ratio). Furthermore, it was co-pulverized with the methanol synthesis catalyst to obtain a catalyst in fine powder form, similar to Example 5.

EXAMPLES 7, 13, 14

Using 19.0 g copper nitrate ($Cu(NO_3)_2 \cdot 3H_2O$) instead of 15.7 g of copper acetate, CuO—$Al_2O_3$ catalyst was prepared by the same method as Example 5. The catalyst obtained was CuO:$Al_2O_3$=6.2:93.8 (weight ratio). Furthermore, it was co-pulverized with the methanol synthesize catalyst to obtain a catalyst in fine powder form, similar to Example 5.

EXAMPLES 8, 15, 16

Using 38.0 g of copper nitrate ($Cu(NO_3)_2 \cdot 3H_2O$) instead of 15.7 g of copper acetate, CuO—$Al_2O_3$ catalyst was prepared by the same method as Example 5. The catalyst obtained was CuO:$Al_2O_3$=11.6:88.4 (weight ratio). Furthermore, it was co-pulverized with the methanol synthesis catalyst to obtain a catalyst in fine powder form similar to Example 5.

COMPARATIVE EXAMPLE 2

Using 50 g of $Al_2O_3$ instead of 50 g of CuO—$Al_2O_3$ catalyst, a catalyst in fine powder form was obtained by co-pulverizing with the methanol synthesis catalyst similar to Example 5.

II. Activation Method of Catalyst and Reaction Method 30 g of n-hexadecane was placed into an autoclave having an internal volume of 100 ml, and 3.7 g of the above fine powder catalyst was added thereto, suspended, and then sealed. Subsequently, while a mixed gas composed of hydrogen, carbon monoxide and nitrogen ($H_2$:CO:$N_2$=1:1:9, molar ratio) was streamed in the autoclave at a flow rate about 240 ml/min., temperature was elevated gradually for several hours from room temperature to 220° C. Simultaneously, the concentration of nitrogen in the mixed gas was decreased gradually up to 0 at the last. The conditions were maintained for about 3 hours at 220° C. to activate the catalyst.

The reaction was conducted under the conditions at a prescribed reaction temperature, 30 kg/cm²-G of reaction pressure and 1000 rpm of rotation frequency of stirring by streaming mixed gas of hydrogen and carbon monoxide at a $H_2$/CO molar ratio of 1 at a flow rate of 345 ml/min. (converted into normal temperature and normal pressure).

Reaction products and unreacted materials obtained by the above operations were analyzed by gas chromatography.

III. Reaction Conditions and Experimental Results

Reaction conditions and experimental results are shown in Tables 1 to 6.

TABLE 1

|  | Example 1 | Example 2 | Example 3 | Example 4 | Comparative 1 |
|---|---|---|---|---|---|
| Reaction conditions |  |  |  |  |  |
| Temperature (°C.) | 280 | 280 | 300 | 320 | 280 |
| Pressure (kg/cm$^2$-G) | 30 | 30 | 30 | 30 | 30 |
| H$_2$/CO (mol. ratio) | 1 | 1 | 1 | 1 | 1 |
| W/F (g-cat · h/mol) | 8 | 4 | 4 | 4 | 4 |
| Results of Reaction |  |  |  |  |  |
| CO Conversion (%) | 60.1 | 41.5 | 44.2 | 43.2 | 33.3 |
| *Yield |  |  |  |  |  |
| Dimethyl Ether | 42.8 | 30.3 | 32.3 | 31.5 | 23.1 |
| Methanol | 2.1 | 1.4 | 0.9 | 0.5 | 0.9 |
| Hydrocarbon | 0.8 | 0.5 | 0.8 | 1.9 | 0.1 |
| CO$_2$ | 14.4 | 9.3 | 10.2 | 9.2 | 10.2 |

*C-mol %

The H$_2$O conversion was calculated by the following formula.

$$H_2O \text{ conversion (\%)} = \frac{CO_2 \text{ production rate (C-mol/g-cat} \cdot h)}{1/2 \text{ dimethyl ether production rate (C-mol/gcat} \cdot h)} \times 100$$

TABLE 2

|  | Example 5 | Example 6 | Example 7 | Example 8 | Comparative 2 |
|---|---|---|---|---|---|
| Reaction conditions |  |  |  |  |  |
| Temperature (°C.) | 280 | 280 | 280 | 280 | 280 |
| Pressure (kg/cm$^2$-G) | 30 | 30 | 30 | 30 | 30 |
| H$_2$/CO (mol. ratio) | 1 | 1 | 1 | 1 | 1 |
| W/F (g-cat · h/mol) | 4 | 4 | 4 | 4 | 4 |
| Results of Reaction |  |  |  |  |  |
| CO Conversion (%) | 51.9 | 49.1 | 41.0 | 47.3 | 37.8 |
| *Yield |  |  |  |  |  |
| Dimethyl Ether | 34.8 | 30.8 | 26.4 | 29.1 | 30.7 |
| Methanol | 3.0 | 2.7 | 2.0 | 2.8 | 1.1 |
| Hydrocarbon | 0.3 | 1.1 | 1.1 | 1.4 | 0.3 |
| CO$_2$ | 13.8 | 14.5 | 11.5 | 14.1 | 5.6 |
| H$_2$O Conversion (%) | 79.2 | 94.3 | 86.6 | 96.7 | 36.2 |

*C-mol %

TABLE 3

|  | Example 5 | Example 9 | Example 10 |
|---|---|---|---|
| Reaction conditions |  |  |  |
| Temperature (°C.) | 280 | 250 | 300 |
| Pressure (kg/cm$^2$-G) | 30 | 30 | 30 |
| H$_2$/CO (mol. ratio) | 1 | 1 | 1 |
| W/F (g-cat · h/mol) | 4 | 4 | 4 |
| Results of Reaction |  |  |  |
| CO Conversion (%) | 51.9 | 45.1 | 45.1 |
| *Yield |  |  |  |
| Dimethyl Ether | 34.4 | 32.2 | 26.7 |
| Methanol | 2.5 | 2.8 | 2.1 |
| Hydrocarbon | 1.2 | 0.2 | 1.9 |
| CO$_2$ | 13.8 | 10.1 | 13.3 |
| H$_2$O Conversion (%) | 79.2 | 62.7 | 99.6 |

*C-mol %

TABLE 4

|  | Example 6 | Example 11 | Example 12 |
|---|---|---|---|
| Reaction conditions |  |  |  |
| Temperature (°C.) | 280 | 250 | 300 |
| Pressure (kg/cm$^2$-G) | 30 | 30 | 30 |
| H$_2$/CO (mol. ratio) | 1 | 1 | 1 |
| W/F (g-cat · h/mol) | 4 | 4 | 4 |
| Results of Reaction |  |  |  |
| CO Conversion (%) | 49.1 | 46.6 | 46.4 |
| *Yield |  |  |  |
| Dimethyl Ether | 30.8 | 29.4 | 28.0 |
| Methanol | 2.7 | 5.0 | 2.3 |
| Hydrocarbon | 1.1 | 0.3 | 2.2 |
| CO$_2$ | 14.5 | 12.0 | 13.9 |
| H$_2$O Conversion (%) | 94.3 | 81.3 | 98.9 |

*C-mol %

TABLE 5

|  | Example 7 | Example 13 | Example 14 |
|---|---|---|---|
| Reaction conditions |  |  |  |
| Temperature (°C.) | 280 | 250 | 300 |
| Pressure (kg/cm$^2$-G) | 30 | 30 | 30 |
| H$_2$/CO (mol. ratio) | 1 | 1 | 1 |
| W/F (g-cat · h/mol) | 4 | 4 | 4 |
| Results of Reaction |  |  |  |
| CO Conversion (%) | 41.0 | 30.1 | 41.6 |
| *Yield |  |  |  |
| Dimethyl Ether | 26.4 | 20.6 | 25.4 |
| Methanol | 2.0 | 2.2 | 1.9 |
| Hydrocarbon | 1.2 | 0.2 | 2.4 |
| CO$_2$ | 11.5 | 7.2 | 11.9 |
| H$_2$O Conversion (%) | 86.6 | 70.0 | 93.9 |

*C-mol %

TABLE 6

|  | Example 8 | Example 15 | Example 16 |
|---|---|---|---|
| Reaction conditions |  |  |  |
| Temperature (°C.) | 280 | 250 | 300 |
| Pressure (kg/cm$^2$-G) | 30 | 30 | 30 |
| H$_2$/CO (mol. ratio) | 1 | 1 | 1 |
| W/F (g-cat · h/mol) | 4 | 4 | 4 |
| Results of Reaction |  |  |  |
| CO Conversion (%) | 47.3 | 41.7 | 45.3 |
| *Yield |  |  |  |
| Dimethyl Ether | 29.1 | 25.0 | 26.8 |
| Methanol | 2.8 | 4.6 | 2.2 |
| Hydrocarbon | 1.4 | 0.4 | 2.2 |
| CO$_2$ | 14.1 | 12.5 | 13.3 |
| H$_2$O Conversion (%) | 96.7 | 99.9 | 99.3 |

*C-mol %

Industrial Applicability

In the method of the invention, the yield of dimethyl ether is high, and the conversion water produced through reaction to hydrogen is high. There is not problem of clogging with catalyst, and mechanical strength is not required. Besides, inexpensive powder catalyst is usable, and taking out of and loading catalyst into a reactor can be conducted easily. Furthermore, removal and recovery of reaction heat and control of reaction temperature are easy. Furthermore, the applicable range of the ratio of carbon monoxide and hydrogen is wide and the reaction is possible in the presence of carbon dioxide in a high concentration. Moreover, affects by impurities and catalyst poisons are small. Consequently, the invention has a great industrial applicability.

We claim:

1. A method of producing dimethyl ether which comprises streaming a mixed gas containing carbon monoxide and either or both of hydrogen and water vapor or a mixed gas of them further containing carbon dioxide into a slurry of a mixed catalyst suspended in a solvent, wherein the mixed catalyst comprises a mixture of zinc oxide, copper oxide and alumina, and is prepared by co-pulverizing to a degree of pulverization of about 0.1 to 20 μm in grain size.

2. The method described in claim 1 wherein the catalyst further contains chrominum oxide.

3. A method of producing dimethyl ether which comprises streaming a mixed gas containing carbon monoxide and either or both of hydrogen and water vapor or a mixed gas of them further containing carbon dioxide into a slurry of a catalyst suspended in a solvent, wherein the catalyst is composed of a methanol synthesis catalyst and a copper oxide carried on an alumina catalyst, and is prepared by co-pulverizing to a degree of pulverization of about 0.1 to 20 μm in grain size.

* * * * *